(12) United States Patent
Lauten-Schlaeger et al.

(10) Patent No.: US 7,155,934 B2
(45) Date of Patent: Jan. 2, 2007

(54) METHOD FOR THE PRODUCTION OF BOROSILICATE GLASS WITH A SURFACE SUITABLE FOR MODIFICATION GLASS OBTAINED ACCORDING TO SAID METHOD AND THE USE THEREOF

(75) Inventors: Gerhard Lauten-Schlaeger, Jena (DE); Thomas Kloss, Jena-Cospeda (DE); Sandra Von Fintel, Jena (DE); Klaus Schneider, Apolda (DE)

(73) Assignee: Schott AG, Mainz (DE)

( * ) Notice: Subject to any disclaimer, the term of this patent is extended or adjusted under 35 U.S.C. 154(b) by 112 days.

(21) Appl. No.: 10/494,659

(22) PCT Filed: Nov. 18, 2002

(86) PCT No.: PCT/DE02/04253

§ 371 (c)(1),
(2), (4) Date: May 5, 2004

(87) PCT Pub. No.: WO03/045862

PCT Pub. Date: Jun. 5, 2003

(65) Prior Publication Data

US 2005/0000248 A1    Jan. 6, 2005

(30) Foreign Application Priority Data

Nov. 19, 2001 (DE) ................ 101 56 713

(51) Int. Cl.
C03C 4/00 (2006.01)
C03C 3/089 (2006.01)
C03C 3/091 (2006.01)

(52) U.S. Cl. ................. 65/30.12; 65/32.5; 65/901; 501/65; 501/66

(58) Field of Classification Search ............. 65/30.1, 65/30.11, 30.12, 30.13, 30.14, 32.3, 32.4, 65/32.5, 60.1, 60.3, 134.1, 134.4, 900, 901; 501/53–79
See application file for complete search history.

(56) References Cited

U.S. PATENT DOCUMENTS 3,287,095 A * 11/1966 Procter et al. ............... 65/482
3,912,481 A * 10/1975 Bartholomew et al. .... 65/30.12
3,940,277 A    2/1976 Pierson et al.
5,006,141 A *  4/1991 Chen et al. ..................... 65/27
5,340,778 A *  8/1994 Kloss et al. .................. 501/52
5,374,595 A   12/1994 Dumbaugh
6,380,112 B1 * 4/2002 Kolberg et al. ............... 501/77
2002/0026811 A1  3/2002 Hoyer et al.

FOREIGN PATENT DOCUMENTS

DE    42 18 377 C1    10/1993
DE    197 58 481 C1    6/1999
EP    0 779 252 A     6/1997
WO    99 40038 A      8/1999

OTHER PUBLICATIONS

Database WPI Section CH, Week 200004, Derwent Publications LTD., London, GB, Class L01, AN 2000-047919, XP002248770 & JP 11 310429 A, Nov. 9, 1999.
Database WPI Section CH, Week 200004, Derwent Publications LTD., London, GB, Class L01, AN 2000-0479120 XP0022487771 & JP 1111 310 430 A, Nov. 9, 1999.
J.J. Cras: "Comparison of Chemical Cleaning Methods of Glass . . ." Boisensors & Bioelectronics 14, 1999, pp. 683-688.
Werner Kern: "Cleaning Solutions Based on Hydrogen Peroxide . . ." RCA Rev. 1970, pp. 187-206.
Horst Scholze: Glas, Natur, Struktur Und Eigenschaften, Springer-Verlag Berlin Heidelberg New York London Paris Tokyo, 1988, pp. 160-162.

* cited by examiner

Primary Examiner—Eric Hug
(74) Attorney, Agent, or Firm—Michael J. Striker

(57) ABSTRACT

The method of making borosilicate glass with a surface having reactive SiOH groups on it includes preparing a borosilicate glass melt and dissolving at least 30 mMol per liter of water in the borosilicate glass melt. The borosilicate glass contains from 70 to 87 percent by weight, $SiO_2$; from 7 to 15 percent by weight, $B_2O_3$; from 0 to 8 percent by weight, $Al_2O_3$; from 0 to 8 percent by weight, $Na_2O$ and from 0 to 8 percent by weight of $K_2O$. The borosilicate glass with the easily modified reactive surface can be used as a substrate for chemically covalent immobilization of reactive substances. This substrate can be used to make a biochemical chip, such as a DNA or gene chip, or dirt-proof window glass.

15 Claims, No Drawings

METHOD FOR THE PRODUCTION OF BOROSILICATE GLASS WITH A SURFACE SUITABLE FOR MODIFICATION GLASS OBTAINED ACCORDING TO SAID METHOD AND THE USE THEREOF

BACKGROUND OF THE INVENTION

The present invention relates to the production of borosilicate glass, in particular a borosilicate glass substrate with a surface suitable for modification, and the glass obtained according to the method according to the invention, and the use thereof.

The use of glass as a carrier substrate for a large number of uses is known per se. According to the usual procedure, a desired chemical substrate (modifying agent), such as biomolecules, is immobilized on the glass surface. This is usually carried out using SiOH groups, which are freely available on the glass surface. To obtain a sufficient number or density of modifying agents, the number of reactive SiOH groups must be increased. This can be accomplished, e.g., using treatment in a gas plasma. A further method for increasing the surface reactivity of glass is to treat it with alkali hydroxides, in particular sodium hydroxide. Glass surfaces that have been treated in this manner then react easily with other reagents, and a coated glass surface is obtained. In this manner, it is possible to covalently bond the surfaces of glass with a large number of compounds to obtain certain properties, such as dirt-proof properties, by bonding with silanes, or it is possible to obtain certain reactions, e.g., with biomolecules.

The term "biochip" refers to devices that have a biological or organic material that is immobilized on the solid carrier substrate. Silicon wafers, thin glass plates, plastic or nylon membranes serve as a common carrier substrate for chips of this type. Aluminum has also been used as carrier material. Glass is typically preferred, however, due to its surface properties, low natural fluorescence compared to other plastic materials, and its resistance to chemical substances and temperature stability. It is also resistant to aging. It has been demonstrated, however, that glass also has disadvantages, e.g., a natural fluorescence. The treatment methods described hereinabove are either complex, however, such as plasma treatment, or they result in an unsatisfactorily activated surface.

SUMMARY OF THE INVENTION

The goal of the present invention, therefore, is to provide glass, the surface of which is suitable for modification and is therefore capable of being used as a substrate basis and/or carrier for a large number of applications in which the glass surface must be treated and/or coated with an agent. The glass and/or the surface should be resistant to aging.

Another goal of the present invention is to provide a method with which glass of this nature is capable of being obtained in this manner in a highly reproducible fashion. Finally, the goal of the present invention is to produce glass of this nature that exhibits only minimal fluorescence when used in the typical optical techniques.

This goal is achieved with the method according to the invention as defined in the claims. Preferred embodiments are defined in the subclaims.

A surprising discovery was that the goal on which the invention is based may be achieved by adding water to melted borosilicate glass. The water of crystallization of the starting materials, in particular, is a preferred water source.

According to the invention, boric acid is used particularly preferably as the source for boroxide.

The method according to the invention is carried out preferably in the presence of aqueous water in a strongly hydrous atmosphere. The melt is typically brought in contact with the hydrous atmosphere. The hydrous atmosphere used in the method according to the invention is capable of being produced in various ways. The preferred procedure is to heat the glass melt in the chamber with fossil fuels, whereby combustion is induced using pure oxygen instead of air (the "oxyfuel technique"). In principle, it is also possible according to the invention, however, to heat the melt using other technical means and to introduce gaseous water into the atmosphere.

A further possibility for increasing the water content in the melt is described in publication DE-A 100 43 454, for example. According to said publication, the oxygen that is released during refinement can be transferred on platinum pipes—which have been rinsed with hydrogen or water vapor—to water that is dissolved in the glass melt.

In a further embodiment that is preferred according to the invention, a glass body is melted only on the surface, in a hydrous atmosphere. A sufficient amount of water also dissolves in the melted glass surface. It was a surprise to discover, according to the invention, that a well-modifiable surface may also be produced easily and conveniently in this manner.

With the method according to the invention, it is possible to provide borosilicate glass that contains at least 30 mMol/liter dissolved water molecules. At least one portion of the water is thereby chemically bound in the $SiO_2$ network, and reactive SiOH groups are formed.

Typically, however, glass that is treated in this manner contains at least 35 mMol/liter, and at least 40 mMol/liter water is particularly preferred in most cases. This means that the quantity of OH groups that is present is at least 60, usually at least 70 and, mostly, at least 80 mMol/liter. In the method according to the invention it is also possible, however, to easily create a higher concentration of reactive OH groups by increasing the water-gas atmosphere or, using the methods described previously, by reacting the oxygen that is present in the melt on platinum pipes rinsed with hydrogen to form water and/or OH groups. Advantageous upper limits of the water content are 75 mMol/liter, in particular 70 mMol/liter, and 65 mMol/liter and/or 60 mMol/liter are particularly preferred. The range of 40 to 60 mMol/liter is most particularly preferred.

In this manner, it is immediately possible to provide glasses that are available, as a substrate, for modification, and that usually have at least 1,500 reactive spots/$cm^2$ surface. The glasses produced according to the invention typically contain so many reactive OH groups capable of binding that at least 3,000, usually at least 4,000, and regularly 5,000 coating and/or modification molecules per square centimeter can be bound on the glass surface. Coating densities with spots of 7,000 to 8,000, even up to 10,000 molecules per square centimeter are possible with the glasses according to the invention. Coatings having thicknesses such as these may be applied easily using printing techniques that are known per se. Ink-jet printers are a preferred technique.

According to the invention, it is preferable to produce glasses of this type as float glass. In this manner, glasses can be provided that have a highly reactive surface and a roughness of greater than 10 nm, and usually greater than 20 nm. Glasses of this type usually have a surface roughness of 150 nm. The high reactivity of glasses according to the invention is that much more surprising because—as described in publication WO 99/40038, for example—it had been assumed that glasses of this type must have a surface roughness of less than 10 nm.

With the method according to the invention it is possible to achieve an increase in surface reactivity with borosilicate glasses. If hydrogen is also added to the method, as in the case of float glass, to prevent oxidation of the tin surface, then the oxygen content that is present in the float bath atmosphere is also reduced to water. As a result, the concentration of water gas that penetrates the melted glass and/or the floated glass is increased further. A preferred float atmosphere contains an inert gas, such as $N_2$, He, etc., and a gaseous reductant, such as $H_2$.

Inert gas is present in an amount of 80 to 85 percent by volume, and the reduction gas is present in an amount of 5 to 15 percent by volume.

Borosilicate glass is a preferred glass according to the invention. Preferred borosilicate glass has a composition of 70 to 85 and/or up to 87 percent by weight of $SiO_2$, 7 to 15 percent by weight of $B_2O_3$, 1.5 to 7 percent by weight of $Al_2O_3$, 2 to 6 percent by weight of $Na_2O$, and 0 to 3 percent by weight of $K_2O$. The amount of $SiO_2$ is typically 78 to 83 percent by weight, and 79 to 82 percent by weight is preferred. The content of $B_2O_3$ is typically 10 to 14 and preferably 11 to 13.3 percent by weight. The content of $Al_2O_3$ is typically between 1.5 and 3 percent by weight, and preferably between 1.8 and 2.6 percent by weight. The content of $Na_2O$ is typically 2.8 to 5 percent by weight, and 3 to 4.5 percent by weight is preferred. Finally, the content of $K_2O$ in the borosilicate glass according to the invention is 0 to 1.5 percent by weight, and 0 to 1.2 percent by weight is particularly preferred. In a particularly preferred embodiment, the glass contains 80 to 81.5 percent by weight of $SiO_2$, 12 to 12.9 percent by weight of $B_2O_3$, 2.1 to 2.4 percent by weight of $Al_2O_3$, and 3.2 to 4.1 percent by weight of $Na_2O$ and 0 to 0.95 percent by weight of $K_2O$. For the borosilicate glass that is preferred according to the invention it has proven advantageous when the sum of $Na_2O$ and $K_2O$ is at least 2.5 percent by weight and a maximum of 8 percent by weight. The minimum amount of both alkali oxides is typically at least 3 percent by weight and a maximum of 5 percent by weight, however, whereby at least 3.8 and a maximum of 4.5 percent by weight is preferred. Particularly preferably, the sum of alkali oxides is at least 4 percent by weight and a maximum of 4.25 percent by weight. In glasses of this nature, $SiO_2$ is the network former.

The method according to the invention can also be carried out with borosilicate glasses that contain alkaline-earth oxides. However, it is preferably carried out on glasses that contain no alkaline-earth oxides or only slight amounts thereof, i.e., impurities only.

Preferably, the borosilicate glasses used in the method according to the invention contain no toxic refining oxides of the fifth main group with polyvalent ionic character, such as $As_2O_3$ or $Sb_2O_3$.

In addition, it has been demonstrated that borosilicate glasses that contain no iron have particularly good transmission properties; this is necessary for a large number of applications that use glass substrates, such as microarrays and biochips.

It was also found that, by selecting the appropriate raw materials for producing the glass, the concentration of iron, in particular $Fe^{3+}$ ions, such as $Fe_2O_3$, may be easily reduced to <0.015 percent by weight (150 ppm). This enables glass to be obtained that exhibits extremely low natural fluorescence. Glasses are obtainable in this manner that have high transparency in the ultraviolet range, particularly in the UVB/UVA wavelength. For example, transmission values of >90% at a wavelength of 360 nm are achieved with floated standard thicknesses of only 0.7 mm to 7 mm. Even at wavelengths of 300 nm, transmission values of 70% can still be achieved with thicknesses of 0.7 to 1 mm.

In a particularly preferred embodiment, the glass according to the invention contains a concentration of octahedrally bound $Fe^{3+}$ ions of <10 ppm, and a concentration of $Cr^{3+}$ of <10 ppm, preferably <5 ppm and, particularly, <2 ppm. The borosilicate glass obtained according to the invention also exhibits an extremely low natural fluorescence and therefore enables improved detection and error-free evaluation of signals that are emitted from fluorescent dyes, which are typically used today as fluorescent markers. The working range of instruments and/or markers of this nature is the wavelength range of 488 nm to 633 nm. The glass is low-fluorescence, i.e., it has such a low natural fluorescence that, in the typical working range, it emits no noticeable natural fluorescence or no natural fluorescence that interferes with the test.

According to the invention, it has also been demonstrated that the procedure according to the invention eliminates the need to provide substrate glasses that are free of alkali ions, as described in publication WO 99/40038, for example. Surprisingly, it has also been demonstrated that, with glasses that are produced using the method according to the invention, the diffusion of sodium ions into the functional layers, which is described there, does not take place.

The glasses produced according to the invention exhibit a high chemical resistance to acids and lyes, in particular alkaline lyes. They have long-term stability as well, which also allows them to be coated easily with a high dot and/or spot density after long-term storage.

Using the method according to the invention, in particular for production using the float method, a substrate glass is obtained that has very flat, fire-polished surfaces with a mean waviness in the range of 0.08 μm on the underside, and 0.11 μm on the top side. Non-porous, smooth surfaces of this nature prove particularly advantageous for hybridization procedures.

The method according to the invention is capable of being used on all common borosilicate glasses. Their production is known to one skilled in the art, and it can be obtained, for example, by melting a batch of quartz sand ($SiO_2$), hydrated sodium tetraborate ($Na_2B_4O_7$), potassium nitrate, aluminum hydroxide and common salt as the refining agent. A typical mixture contains 70 to 87 percent by weight of $SiO_2$, 7 to 15 percent by weight of $B_2O_3$, 0 to 8, and particularly 1 to 8, percent by weight of $Al_2O_3$, 1 to 8 percent by weight of $Na_2O$, 0.1 to 8 percent by weight of $K_2O$, and, if necessary, 0.1 to 8 percent by weight of other components. If necessary, the $SiO_2$ content can also be reduced to 62 or 64 percent by weight, as long as the $SiO_2$ still functions as a network former. In individual cases, up to 6 percent by weight of $SnO_2$, up to 4 percent by weight of $TiO_2$, and slight amounts, i.e., up to 0.1 percent by weight, of $Sb_2O_3$ can be present.

Glass of this type that is obtained according to the invention can be coated in a manner known per se. According to the typical procedure, the glass surface is first cleaned. Any salts on the surface are removed. Various cleaning methods can be used here. The cleaning procedure includes treatment with alkaline, acidic and/or organic media. A type of cleaning that is used often is the "Kern cleaning method", in which rinsing is first carried out using alkaline and oxidizing solutions at elevated temperatures, followed by rinsing with water at room temperatures, then aftertreatment with acids is carried out at elevated temperatures (W. Kern and D. A. Puotinen: Cleaning solutions based on hydrogen peroxide for use in silicon semi-conductor technology, RCA Rev. (1970) 187–206). After rinsing with water, a glass surface is obtained that can be used to immobilize the most diverse types of reagents. A summary of cleaning methods of this type, e.g., by J. J. Cras, C. A. Rowe-Taitt, D. A. Nievens and F. S. Ligler, is described in "Comparison of chemical cleaning methods of glass in preparation for silanization" in Biosensors & Bioelectronics 14 (1999) 683–688. After cleaning, in particular, the glasses obtained according to the invention are usually coated with a particular desired substance by covalently bonding reactive and/or functional groups of the substance to the surface via chemical reaction with the SiOH groups of the glass.

The present invention also relates to borosilicate glass and/or a borosilicate glass substrate that is obtained using the method according to the invention, and that has a reactive OH group density of at least 30 mMol/liter, at least on its surface. It is preferably planar glass, in particular a flat glass such as float glass.

The present invention also relates to the use of glasses of this type for the chemically covalent immobilization of reactive substances, in particular to produce sensors and biochips, dirt-proof glasses, in particular window glasses, such as Duran®, laboratory glasses, reagent glasses, and microarrays, such as electronic noses and/or artificial nose chips, electronic tongues, chips for the polymerase-chain reaction, DNA-microarray chips and/or gene chips, protein chips, and "biochemical laboratories" on a chip. Chips of this nature are also used in the diagnosis and analysis of samples, and labelled samples in particular, such as fluorescence-, color-, or radioisotope-labelled samples, and in gas and smoke alarms. The glasses coated in accordance with the invention are also suited for use in sensors in the automotive industry, such as pressure, rollover and skid sensors. The invention will be described in greater detail briefly using the following examples.

EXAMPLES

The appropriate starting materials were fused together to melt borosilicate glasses that conform with the standard EN 1748-1. The glasses were refined with common salt during melting. The borosilicate glass that was melted in this manner was then poured into a float system to form flat glass. Thin-glass substrates with a thickness of 0.7 mm, 1.1 mm, 2 mm, 3 mm and 5 mm were produced in this manner. By selecting the appropriate raw materials, the floated borosilicate glass contained $Fe_2O_3$ in an amount <150 ppm. The following glasses were produced in this manner.

|  | Composition of Example 1 | Composition of Example 2 | Composition of Example 3 | Composition of Example 4 | Composition of Example 5 | Composition of Example 6 | Composition of Example 7 | Composition of Example 8 | Composition of Example 9 |
|---|---|---|---|---|---|---|---|---|---|
| $SiO_2$ | 80.7 | 80.6 | 80.6 | 80.2 | 81.0 | 81.2 | 80.8 | 79.00 | 78.5 |
| $B_2O_3$ | 12.7 | 12.9 | 12.9 | 12.7 | 12.3 | 12.0 | 12.6 | 10.50 | 10.30 |
| $Al_2O_3$ | 2.4 | 2.25 | 2.25 | 2.10 | 2.3 | 2.2 | 2.2 | 4.30 | 4.50 |
| $Na_2O$ | 3.5 | 3.2 | 4.05 | 3.60 | 4.0 | 4.1 | 3.8 | 4.70 | 4.50 |
| $K_2O$ | 0.6 | 0.95 | — | 0.60 | — | — | 0.4 | 1.00 | 0.70 |
| $Fe_2O_3$ | <0.015 | <0.015 | <0.015 | <0.015 | <0.015 | <0.015 | <0.015 | <0.015 | <0.015 |
| $\rho$ g cm$^{-3}$ | 2.22 | 2.23 | 2.23 | 2.23 | 2.22 | 2.22 | 2.22 | 2.27 | 2.28 |
| $\alpha$ 10$^{-6}$ K$^{-1}$ | 3.25 | 3.35 | 3.32 | 3.34 | 3.23 | 3.27 | 3.20 | 4.11 | 4.06 |
| Tg °C. | 528 | 530 | 534 | 515 | 516 | 541 | 530 | 563 | 570 |
| OKP °C. | 560 | 562 | 556 | 552 | 556 | 565 | 560 | 586 | 599 |
| EW °C. | 825 | 830 | 815 | 820 | 832 | 835 | 820 | 830 | 838 |
| VA °C. | 1265 | 1250 | 1245 | 1258 | 1266 | 1267 | 1240 | 1271 | 1286 |
| $T_{300\,nm}$ | 30.0 | 30.0 | 30.0 | 30.0 | 30.0 | 30.0 | 30.0 | 30.0 | 30.0 |

The glasses obtained in this manner were than investigated with regard for their transmission properties. It was shown that the glasses obtained in this manner have high transparency in the UVB and UVA wavelength range. At a wavelength of 360 nm, transmission values of 90% are still obtained for the standard thicknesses mentioned previously. At a wavelength of 300 nm, the glasses mentioned hereinabove still achieve a transmission value of >70% at a thickness of 1 mm. In addition, the glasses according to the invention exhibit a slight, i.e., barely noticeable, solarization, so that radiation damage and/or errors in light permeability caused by solarization when strong irradiation occurs at the wavelengths typically used can be disregarded. In addition, the glasses according to the invention exhibit an only slight fluorescence behavior.

Before use, the surfaces of the substrate glasses according to the invention are cleaned of organic and anorganic contaminants. A cleaning procedure of this nature is preferred for the derivatization of the surfaces. In this context, it has been demonstrated that the "Kern cleaning method", which is known from semiconductor technology, is particularly suited for the glasses according to the invention (W. Kern and D. A. Puotinen: Cleaning solutions based on hydrogen peroxide for use in silicon semi-conductor technology, RCA Rev. (1970) 187–206).

What is claimed is:

1. A method of producing borosilicate glass with an easily modified surface, said easily modified surface having reactive SiOH groups thereon, said method comprising the steps of;
   a) making a glass melt comprising a borosilicate glass; and
   b) dissolving at least 30 mMol of water in said glass melt per liter of said glass melt;
   wherein said borosilicate glass comprises from 70 to 87 percent by weight of $SiO_2$, from 7 to 15 percent by weight of $B_2O_3$, from 0 to 8 percent by weight of $Al_2O_3$, from 0 to 8 percent by weight of $Na_2O$, from 0 to 8 percent by weight of $K_2O$ and optionally from 0 to 8 percent by weight of additional optional components.

2. The method as defined in claim 1, wherein said water is added to said glass melt via hydrous starting materials.

3. The method as defined in claim 1, wherein said glass melt is brought into contact with a hydrous atmosphere, in order to dissolve said water in said glass melt.

4. The method as defined in claim 3, wherein said hydrous atmosphere is produced by burning fossil fuels with pure oxygen.

5. The method as defined in claim 1, wherein said borosilicate glass is a float glass and said method comprises a float glass making process.

6. The method as defined in claim 1, wherein said borosilicate glass is free of toxic refining agents.

7. The method as defined in claim 1, wherein said borosilicate glass contains alkali ions.

8. The method as defined in claim 1, wherein said borosilicate glass contains less than 150 ppm of $Fe_2O_3$ and less than 5 ppm of $Cr^{+3}$.

9. The method as defined in claim 1, further comprising reacting said reactive SiOH groups on said easily modified surface with reactive groups of at least one substance in order to at least partial coat said surface with said at least one substance.

10. A borosilicate glass with an easily modified surface, said easily modified surface having reactive SiOH groups thereon, wherein said borosilicate glass is made by a method comprising the steps of:
   a) making a glass melt comprising a borosilicate glass; and
   b) dissolving at least 30 mMol of water in said glass melt per liter of said glass melt;
   wherein said boroslilcate glass comprises from 70 to 87 percent by weight of $SiO_2$, from 7 to 15 percent by weight of $B_2O_3$, from 0 to 8 percent by weight of $Al_2O_3$, from 0 to 8 percent by weight of $Na_2O$, from 0 to 8 percent by weight of $K_2O$ and optionally from 0 to 8 percent by weight of additional optional components.

11. The borosilicate glass as defined in claim 10, wherein said method comprises adding said water to said glass melt via hydrous starting materials.

12. The borosilicate glass as defined in claim 10, wherein said method comprises bringing said glass melt In contact with a hydrous atmosphere, in order to dissolve said water in said glass melt.

13. The borosilicate glass as defined in claim 12, wherein said hydrous atmosphere is produced by burning fossil fuels with pure oxygen.

14. A substrate for chemically covalent immobilization of reactive substances, said substrate comprising a borosilicate glass with an easily modified surface, said easily modified surface having reactive SiOH groups thereon, wherein said borosilicate glass is made by a method comprising the steps of:
   a) making a glass melt comprising a borosilicate glass; and
   b) dissolving at least 30 mMol of water in said glass melt per liter of said glass melt;
   wherein said borosilicate glass comprises from 70 to 87 percent by weight of $SiO_2$, from 7 to 15 percent by weight of $B_2O_3$, from 0 to 8 percent by weight of $Al_2O_3$, from 0 to 8 percent by weight of $Na_2O$, from 0 to 8 percent by weight of $K_2O$ and optionally from 0 to 5 percent by weight of additional optional components.

15. A sensor, biochip, dirt-proof working glass for a window, reagent glass, laboratory glass, micro-array, electronic nose, artificial nose chip, electronic tongue, chip for polymerase-chain reaction, DNA micro-array chip, gene chip, protein chip or a biochemical laboratory chip comprising said substrate as defined in claim 14.

* * * * *